United States Patent
Brown et al.

(10) Patent No.: US 11,384,956 B2
(45) Date of Patent: Jul. 12, 2022

(54) MODULAR FAN ASSEMBLY WITH ARTICULATING NOZZLE

(71) Applicant: SharkNinja Operating, LLC, Needham, MA (US)

(72) Inventors: Andre D. Brown, Natick, MA (US); Jason B. Thorne, Wellesley Hills, MA (US); Peter Hutchinson, Suzhou (CN); Gary Palladino, Sommerville, MA (US); Alden Kelsey, Newton Upper Falls, MA (US); Daniel J. Innes, West Roxbury, MA (US); Zach Hellman, Needham, MA (US)

(73) Assignee: SharkNinja Operating LLC, Needham, MA (US)

(*) Notice: Subject to any disclaimer, the term of this patent is extended or adjusted under 35 U.S.C. 154(b) by 106 days.

(21) Appl. No.: 15/986,377

(22) Filed: May 22, 2018

(65) Prior Publication Data
US 2018/0335228 A1    Nov. 22, 2018

Related U.S. Application Data

(60) Provisional application No. 62/509,711, filed on May 22, 2017.

(51) Int. Cl.
*F24F 13/20* (2006.01)
*F04D 29/40* (2006.01)
(Continued)

(52) U.S. Cl.
CPC .............. *F24F 13/20* (2013.01); *A61L 9/032* (2013.01); *A61L 9/035* (2013.01); *A61L 9/122* (2013.01);
(Continued)

(58) Field of Classification Search
CPC .......... F24F 13/20; F24F 3/1603; F24F 7/007; F24F 11/79; F24F 11/0008; F24F 6/12;
(Continued)

(56) References Cited

U.S. PATENT DOCUMENTS 7,931,449 B2   4/2011   Fitton et al.
7,972,111 B2   7/2011   Crawford et al.
(Continued)

*Primary Examiner* — Sean E Conley
*Assistant Examiner* — Brendan A Hensel
(74) *Attorney, Agent, or Firm* — Mintz Levin Cohn Ferris Glovsky and Popeo, PC; Lisa Adams

(57) ABSTRACT

An air treatment system is disclosed that includes a modular configuration whereby a fan module, filter module, and humidifier module may couple together to provide a plurality of air treatment solutions. In more detail, the modules can stack end-to-end in a vertical configuration. The modules may electrically couple to each other via a common electrical bus and enable a controller disposed in the fan module (or other module) to control fan flow rates, direction, and humidity. The fan module can include an articulating nozzle capable of directing airflow in virtually any direction and angle about an environment. The fan module can further include an inlet arrangement that can selectively restrict external air from entering the fan module housing when the fan module is fluidly coupled to the filter module. Thus, the fan module may generate air flow from exclusively filtered air to minimize or otherwise reduce bacterial/mold growth within the fan module housing.

20 Claims, 13 Drawing Sheets

(51) Int. Cl.
  *F24F 6/12* (2006.01)
  *F24F 11/00* (2018.01)
  *A61L 9/14* (2006.01)
  *F24F 11/79* (2018.01)
  *F24F 7/007* (2006.01)
  *F04D 25/08* (2006.01)
  *F04D 29/70* (2006.01)
  *A61L 9/03* (2006.01)
  *A61L 9/12* (2006.01)
  *F24F 8/10* (2021.01)
  *F24F 13/28* (2006.01)
  *F24F 120/12* (2018.01)

(52) U.S. Cl.
  CPC ............... *A61L 9/125* (2013.01); *A61L 9/14* (2013.01); *F04D 25/08* (2013.01); *F04D 29/403* (2013.01); *F04D 29/703* (2013.01); *F24F 6/12* (2013.01); *F24F 7/007* (2013.01); *F24F 8/10* (2021.01); *F24F 11/0008* (2013.01); *F24F 11/79* (2018.01); *A61L 2209/111* (2013.01); *A61L 2209/13* (2013.01); *A61L 2209/14* (2013.01); *A61L 2209/16* (2013.01); *F24F 13/28* (2013.01); *F24F 2013/205* (2013.01); *F24F 2120/12* (2018.01); *F24F 2221/36* (2013.01); *F24F 2221/38* (2013.01)

(58) Field of Classification Search
  CPC ............ F24F 2013/205; F24F 2221/38; F24F 2221/36; F24F 2120/12; F24F 13/28; A61L 9/125; A61L 9/035; A61L 9/122; A61L 9/032; A61L 9/14; A61L 2209/111; A61L 2209/16; A61L 2209/13; A61L 2209/14; F04D 29/703; F04D 25/08; F04D 29/403
  See application file for complete search history.

(56) References Cited

U.S. PATENT DOCUMENTS

| | | |
|---|---|---|
| 8,052,379 B2 | 11/2011 | Gammack |
| 8,092,166 B2 | 1/2012 | Nicolas et al. |
| 8,197,226 B2 | 6/2012 | Fitton et al. |
| 8,246,317 B2 | 8/2012 | Gammack |
| 8,308,432 B2 | 11/2012 | Crawford et al. |
| 8,308,445 B2 | 11/2012 | Gammack et al. |
| 8,348,596 B2 | 1/2013 | Gammack |
| 8,348,597 B2 | 1/2013 | Gammack |
| 8,348,629 B2 | 1/2013 | Fitton et al. |
| 8,356,804 B2 | 1/2013 | Fitton et al. |
| 8,366,403 B2 | 2/2013 | Wallace et al. |
| 8,403,640 B2 | 3/2013 | Gammack et al. |
| 8,403,650 B2 | 3/2013 | Gammack et al. |
| 8,408,869 B2 | 4/2013 | Hutton et al. |
| 8,430,624 B2 | 4/2013 | Cookson et al. |
| 8,454,322 B2 | 6/2013 | Gammack et al. |
| 8,465,574 B2 | 6/2013 | Horne |
| 8,469,655 B2 | 6/2013 | Gammack |
| 8,469,658 B2 | 6/2013 | Gammack et al. |
| 8,469,660 B2 | 6/2013 | Dyson et al. |
| 8,529,203 B2 | 9/2013 | Crawford et al. |
| 8,551,227 B2 | 10/2013 | Horne |
| 8,613,601 B2 | 12/2013 | Helps |
| 8,708,650 B2 | 4/2014 | Crawford et al. |
| 8,714,937 B2 | 5/2014 | Fitton et al. |
| 8,721,286 B2 | 5/2014 | Gammack et al. |
| 8,721,307 B2 | 5/2014 | Li |
| 8,734,094 B2 | 5/2014 | Wallace et al. |
| 8,764,412 B2 | 7/2014 | Gammack et al. |
| 8,770,946 B2 | 7/2014 | Fitton et al. |
| 8,783,663 B2 | 7/2014 | Fitton et al. |
| 8,784,071 B2 | 7/2014 | Gammack |
| 8,873,940 B2 | 10/2014 | Wallace et al. |
| 8,882,451 B2 | 11/2014 | Fitton et al. |
| 8,894,354 B2 | 11/2014 | Hodgson |
| 8,932,028 B2 | 1/2015 | Fitton et al. |
| 8,967,979 B2 | 3/2015 | Fitton et al. |
| 8,967,980 B2 | 3/2015 | Fitton et al. |
| 9,004,858 B2 | 4/2015 | Nicolas et al. |
| 9,011,116 B2 | 4/2015 | Li |
| 9,062,685 B2 | 6/2015 | Stewart et al. |
| 9,127,689 B2 | 9/2015 | Gammack et al. |
| 9,127,855 B2 | 9/2015 | Staniforth et al. |
| 9,151,299 B2 | 10/2015 | Nock et al. |
| 9,194,596 B2 | 11/2015 | Dyson et al. |
| 9,249,809 B2 | 2/2016 | Nock et al. |
| 9,249,810 B2 | 2/2016 | Gammack et al. |
| 9,283,573 B2 | 3/2016 | Nock et al. |
| 9,291,361 B2 | 3/2016 | Staniforth et al. |
| 9,328,739 B2 | 5/2016 | Atkinson |
| 9,335,064 B2 | 5/2016 | Staniforth et al. |
| 9,366,449 B2 | 6/2016 | Staniforth et al. |
| 9,410,711 B2 | 8/2016 | Wilson et al. |
| 9,458,853 B2 | 10/2016 | Staniforth et al. |
| 9,513,028 B2 | 12/2016 | Gammack et al. |
| 9,534,610 B2 | 1/2017 | Stewart et al. |
| 9,568,006 B2 | 2/2017 | Johnson et al. |
| 9,599,356 B2 | 3/2017 | Staniforth et al. |
| 9,599,368 B2 | 3/2017 | Fitton et al. |
| 9,745,981 B2 | 8/2017 | Dos Reis et al. |
| 9,745,988 B2 | 8/2017 | Hodgson et al. |
| 9,745,996 B2 | 8/2017 | Nurzynski |
| 9,752,789 B2 | 9/2017 | Staniforth et al. |
| 9,797,411 B2 | 10/2017 | Dyson et al. |
| 9,797,413 B2 | 10/2017 | Stewart et al. |
| 9,797,612 B2 | 10/2017 | Staniforth et al. |
| 9,797,613 B2 | 10/2017 | Staniforth et al. |
| 9,816,531 B2 | 11/2017 | Simmonds et al. |
| 9,903,602 B2 | 2/2018 | Darvill |
| 9,926,804 B2 | 3/2018 | Nicolas et al. |
| 9,927,136 B2 | 3/2018 | Staniforth et al. |
| 9,982,677 B2 | 5/2018 | Beavis et al. |
| 10,006,657 B2 | 6/2018 | Gammack et al. |
| 10,036,565 B2 | 7/2018 | Duvall et al. |
| 10,041,504 B2 | 8/2018 | Stewart |
| 10,094,392 B2 | 10/2018 | Poulton et al. |
| 10,094,395 B2 | 10/2018 | Stewart et al. |
| 10,094,581 B2 | 10/2018 | Staniforth et al. |
| 10,100,836 B2 | 10/2018 | Stickney et al. |
| 10,144,561 B2 | 12/2018 | Duvall et al. |
| 10,145,388 B2 | 12/2018 | Simmonds et al. |
| 10,145,573 B2 | 12/2018 | Duvall et al. |
| 10,174,764 B2 | 1/2019 | Johnson et al. |
| 10,202,983 B2 | 2/2019 | Peet et al. |
| 10,221,860 B2 | 3/2019 | Gammack et al. |
| 10,260,521 B2 | 4/2019 | Barclay |
| 10,260,529 B2 | 4/2019 | Hughes et al. |
| 10,304,324 B2 | 5/2019 | Smith et al. |
| 10,309,420 B2 | 6/2019 | Johnson et al. |
| 10,344,773 B2 | 7/2019 | Wallace et al. |
| 10,408,478 B2 | 9/2019 | Staniforth et al. |
| 10,428,837 B2 | 10/2019 | Atkinson et al. |
| 10,465,928 B2 | 11/2019 | Staniforth et al. |
| 10,563,875 B2 | 2/2020 | Staniforth et al. |
| 10,612,565 B2 | 4/2020 | Staniforth et al. |
| 2010/0226749 A1 | 9/2010 | Gammack et al. |
| 2011/0058935 A1 | 3/2011 | Gammack et al. |
| 2011/0236228 A1 | 9/2011 | Fitton et al. |
| 2012/0180655 A1* | 7/2012 | Law ............ F24F 3/1603 95/1 |
| 2013/0234347 A1 | 9/2013 | Staniforth et al. |
| 2013/0280061 A1 | 10/2013 | Stickney |
| 2013/0330238 A1* | 12/2013 | Lee ............ F24F 3/1603 422/123 |
| 2013/0336771 A1 | 12/2013 | Dyson et al. |
| 2014/0020561 A1* | 1/2014 | Aery ............ B01D 46/2411 96/224 |
| 2014/0199185 A1 | 7/2014 | Nicolas et al. |
| 2014/0199186 A1 | 7/2014 | Nicolas et al. |
| 2014/0255173 A1 | 9/2014 | Poulton et al. |

(56) References Cited

U.S. PATENT DOCUMENTS

| | | |
|---|---|---|
| 2014/0294667 A1* | 10/2014 | Sevy ........................ A61L 2/00 |
| | | 422/4 |
| 2015/0233598 A1* | 8/2015 | Shikii ..................... F24F 11/79 |
| | | 165/244 |
| 2016/0032927 A1 | 2/2016 | Johnson et al. |
| 2016/0184753 A1* | 6/2016 | Chu .................. B01D 46/0002 |
| | | 96/74 |
| 2016/0238039 A1* | 8/2016 | Stewart ................ F04D 29/403 |
| 2017/0108011 A1 | 4/2017 | Johnson et al. |
| 2017/0350416 A1 | 12/2017 | Peters |
| 2018/0274815 A1 | 9/2018 | Gammack et al. |
| 2019/0128553 A1* | 5/2019 | Hilbig ..................... F24F 11/30 |
| 2019/0168150 A1 | 6/2019 | Biltcliffe et al. |
| 2019/0168151 A1 | 6/2019 | Biltcliffe et al. |
| 2019/0170157 A1 | 6/2019 | Mogridge et al. |
| 2019/0170162 A1 | 6/2019 | Jennings et al. |
| 2019/0264948 A1* | 8/2019 | Jung ................. B01D 46/0047 |

\* cited by examiner

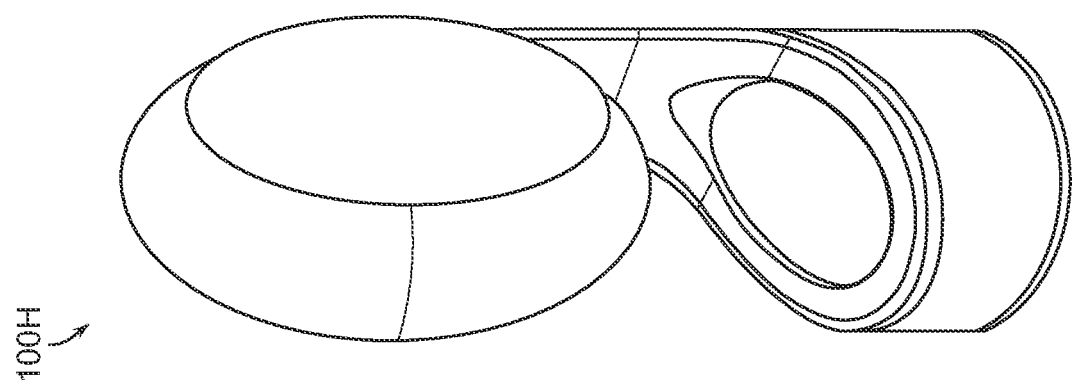
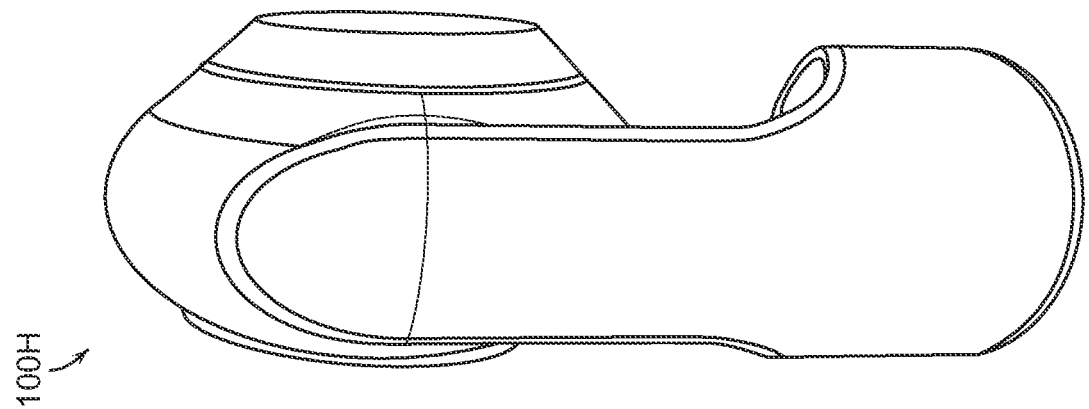
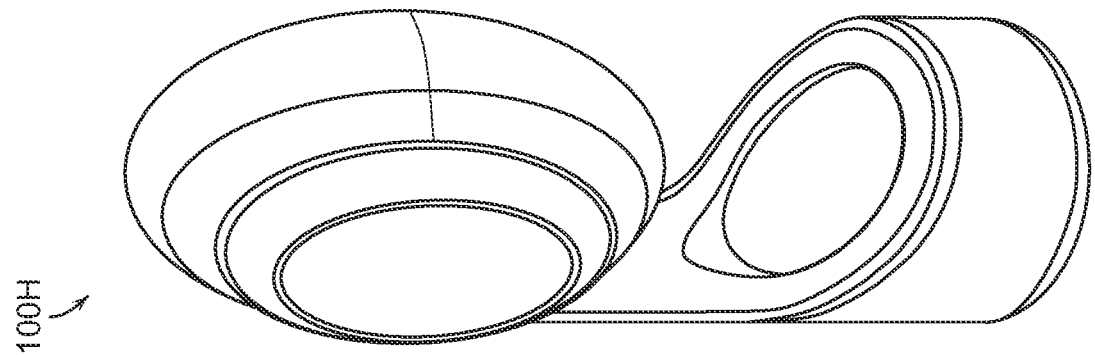

MODULAR FAN ASSEMBLY WITH ARTICULATING NOZZLE

CROSS-REFERENCE TO RELATED APPLICATIONS

This application claims the benefit of U.S. Provisional Patent Application Ser. No. 62/509,711, filed on May 22, 2017 which is fully incorporated herein by reference.

TECHNICAL FIELD

This specification relates generally to air treatment systems, and more particularly, to a modular fan assembly with an articulating nozzle and a modular housing arrangement whereby air treatment assemblies such as the articulating nozzle, humidifier, and air filter may be coupled together to form a stack/tower arrangement to provide multiple air quality treatment solutions within a relatively compact footprint.

BACKGROUND INFORMATION

Fan assemblies generate air flow in various environments such as homes and offices. Fans often include a mechanism that allows a user to redirect air output in a desired location by applying a user-supplied force to rotate/tilt the fan to a desired position. Also, fans often include a feature that allows the fan to horizontally span/sweep right-to-left automatically to target a larger area within a given environment.

Some fan assemblies offer integrated humidification devices which may include a water reservoir proximate to a fan/impeller of the fan assembly. Moisture may then be introduced by exposing the impeller to water droplets/vapor. However, exposure of the impeller and other internal workings of the fan to water vapor/droplets may promote the growth of bacteria/mold. As a result, the fan may then output foul smelling and/or air which is harmful to occupants in the environment. Therefore, while known fan apparatuses are generally effective at increasing air circulation, such fans remain at a fixed position and are unable to adjust to varying conditions in the environment. Moreover, fans may inadvertently circulate air which includes harmful bacterial and/or foul-smelling particles.

BRIEF DESCRIPTION OF THE DRAWINGS

These and other features advantages will be better understood by reading the following detailed description, taken together with the drawings wherein:

FIGS. 14A-14G show an additional example configuration for an air treatment system, in accordance with an embodiment of the present disclosure.

DETAILED DESCRIPTION

As discussed above, fan devices may inadvertently circulate air which includes harmful bacteria and/or foul-smelling particles. Moreover, such fan devices can encourage the internal growth of bacteria and mold on components such as a motor that is used to generate airflow. This can foul both the air quality of an environment, and shorten the overall lifespan of components within the fan device.

In general, the present disclosure is directed to an air treatment system that includes a modular configuration whereby a fan module, filter module, and humidifier module may couple together to provide a plurality of air treatment solutions within a relatively small footprint. In more detail, the fan module, filter module and humidifier module can stack end-to-end in a vertical configuration. The modules may electrically couple to each other via a common electrical bus and enable a controller disposed in the fan module (or other module) to control fan flow rates, direction, and humidity. Note the modules may be configured to operate independent of each other (e.g., when decoupled and separated). The fan module may include an articulating nozzle capable of directing airflow in virtually any direction and angle about an environment. The fan module can further include an intake with an inlet arrangement that can selectively restrict external air from entering the fan module housing when the fan module is fluidly coupled to the filter module. Thus, the fan module may generate air flow from exclusively filtered air to minimize or otherwise reduce bacterial/mold growth within the fan module housing.

The term "coupled" as used herein refers to any connection, coupling, link or the like. Such "coupled" devices are not necessarily directly connected to one another and may be separated by intermediate components or devices.

The term substantially, as generally referred to herein, refers to a degree of precision within acceptable tolerance that accounts for and reflects minor real-world variation due to material composition, material defects, and/or limitations/peculiarities in manufacturing processes. Such variation may therefore be said to achieve largely, but not necessarily wholly, the stated characteristic. To provide one non-limiting numerical example to quantify "substantially," minor variation may cause a deviation of up to and including ±5% from a provided quality/characteristic unless otherwise provided by the present disclosure.

Figure 1:
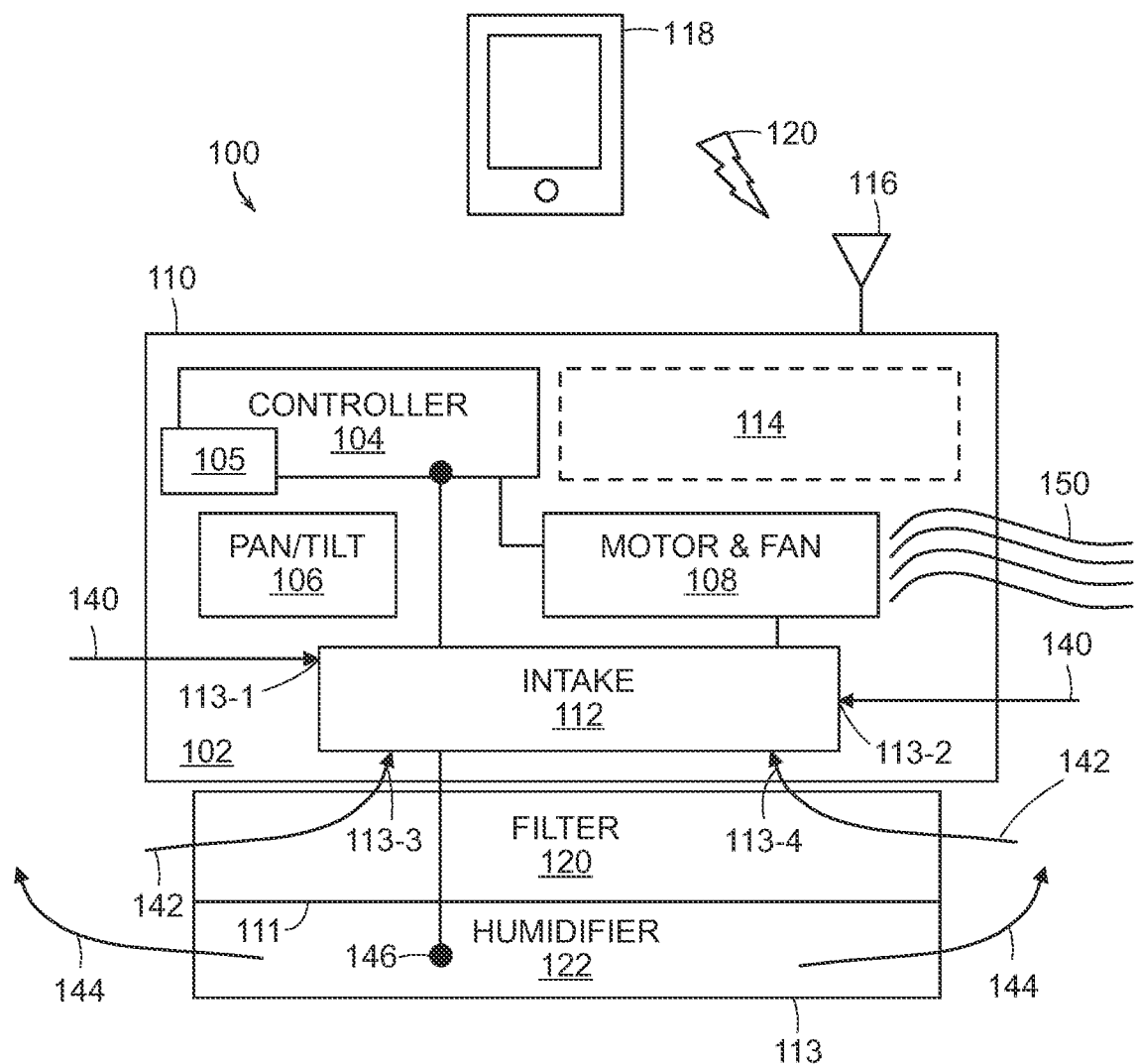
FIG. 1 shows a block diagram of an example air treatment system in accordance with an embodiment of the present disclosure.

Turning now to FIG. 1, one embodiment of an air treatment system 100 is shown in accordance with aspects of the present disclosure. As shown, the air treatment system 100 includes a fan 102 (or fan module 102) removably coupled to an optional air filter 120 (or air filter portion 120), and an optional humidifier 122 (or humidifier portion 122). Note that the optional air filter 120 and the optional humidifier 122 may be coupled in a different order, such as shown in FIGS. 13A-13D where the humidifier 122 is coupled between the filter 120 and the base 240 of the fan module 102. As shown and described, the components of the air treatment system may be coupled end-to-end to form a vertical stack configuration. In the stack configuration, the humidifier module 122 may support the fan module 102 and the filter module 120. The fan module 102, filter module 120 and humidifier 122 may also be referred to as a fan module 102, filter module 120 and humidifier module 122.

The fan module 102 may include a housing 110 formed of a single piece or may optionally comprise a plurality of housing portions. Each of the optional humidifier 122 and the air filter 120 may both electrically and fluidly couple with the fan module 102, although this disclosure is not limited in this regard. For example, and as discussed further below, the humidifier 122 may not necessarily be in direct fluid communication (e.g., via one or more passageways therebetween) and may instead be indirectly fluidly coupled by virtue of the humidifier outputting humidified air externally which may then be received by the fan module via, for instance, inlet ports 113-1 and 113-2. The humidifier 122 may include a plurality of fluid couplings, including air, water, emulsions of air and water, and purified air received from the air filter 120.

The fan module 102 includes a controller 104, a pan/tilt mechanism 106, a motor and fan assembly 108, and an air intake 112. The fan module 102 may also include an antenna device 116. The antenna device 116 (which may also be referred to as a network interface) may be configured to communicate with, for instance, one or more user devices such as the user device 118. The user device 118 may include a so-called "app" for controlling operation of the air treatment system 100, which will be discussed in greater detail below. The fan module 102 may therefore communicate with the user device 118 via a wireless connection 120.

To this end, air treatment system 100 may be configured for close range or long range communication between the fan module 102 and the user device 118. The term, "close range communication" is used herein to refer to systems and methods for wirelessly sending/receiving data signals between devices that are relatively close to one another. Close range communication includes, for example, communication between devices using a BLUETOOTH™ network, a personal area network (PAN), near field communication, ZigBee networks, a Wi-Fi network (e.g., IEE 802.11X) millimeter wave communication, ultra-high frequency (UHF) communication, combinations thereof, and the like. Close range communication may therefore be understood as enabling direct communication between devices, without the need for intervening hardware/systems such as routers, cell towers, internet service providers, and the like.

The controller 104 comprises at least one processing device/circuit such as, for example, a digital signal processor (DSP), a field-programmable gate array (FPGA), Reduced Instruction Set Computer (RISC) processor, x86 instruction set processor, microcontroller, an application-specific integrated circuit (ASIC). The controller 104 may be implemented, for example, using software (e.g., C or C++ executing on the controller/processor 104), hardware (e.g., hardcoded gate level logic or purpose-built silicon) or firmware (e.g., embedded routines executing on a microcontroller), or any combination thereof. The controller 104 may further include a memory 105. The memory 105 may comprise, for example, volatile and/or non-volatile memory. The memory 105 may include operational settings/parameters such as fans speed, heating/cool modes, aromatic selection properties, scheduling, voice recognition profiles, and/or face recognition profiles. Each of the operational settings may be adjusted remotely via the app executed on the user device 118, for instance. The memory 105 may also include air particle quality measurements, and fan schedules. The app may further allow for displaying of data logged from the fan module. Such logged data may include periodic temperature measurements, particle count data, and so on. Note, other modules (e.g., the filter module and the humidifier module) may also include associated controllers and/or memory that enable independent operation. However, the controller 104 may become a "master" controller when the modules are coupled together.

The pan/tilt mechanism 106 may comprise one or more mechanisms for horizontal and/or vertical adjustment of the portion of the housing 110 including the motor and fan 108. For instance, the pan/tilt mechanism 106 may be configured with one or more gears, servos, etc., to adjust the yaw/pitch based on user input (e.g., from the user device 118). Accordingly, the pan/tilt mechanism 106 allows the fan module 102 to adjust both along a horizontal and/or vertical axis to provide up to 360 degrees of motion for each axis thus forming a spherical coverage envelop.

The motor and fan 108 may output air 150 and may be any suitable motor and fan for providing a desired amount of air volume and air flow speed. The motor of the motor and fan 108 may be variable (e.g., a DC stepper motor, or a brushless DC motor) for adjusting fan speed during operation.

The intake 112 may include one or more ducts/passageways for providing air to the motor and fan 108. The intake 112 may include a plurality of intake ports including intake ports 113-1 and 113-2. Intake ports 113-1 and 113-2 may be configured to receive air 140 external to the housing 110. In some cases, the intake ports 113-1 and 113-2 may be disposed on opposite sides of the housing 110.

The intake 112 may further include intake ports 113-3 and 113-4. Intake ports 113-3 and 113-4 may be configured to receive air 142 from the filter 120. In such cases, the air 142 may be accurately referred to as filtered air. In an embodiment, the presence of the filter 120 coupled to the housing 110 causes the intake ports 113-1 and 113-2 to mechanically close. This may be accomplished via an internal damper, valve, closeable vents, or other suitable device. Alternatively, or in addition, the intake ports 113-1 and 113-2 may be closed simply by the presence of a portion of the filter 120 blocking air flow. Therefore, intake ports 113-1 and 113-2 may be entirely closed or at least substantially closed, e.g., restricting input from external air 140 to less than 10%, and preferably, substantially 0%. Thus, the fan module 102 may receive only filtered air 142 for output by the motor and fan 108 when the fan module 102 is coupled to the filter 120. This may advantageously reduce the amount of humidified air from a humidifier or from a surrounding environment that would otherwise enter the fan module 102 and encouraging bacteria and mold growth.

Continuing on, the filter 120 may include a housing 111. The housing 111 may include a portion configured to removably couple to the housing 110 of the fan module 102. The filter 120 may include, for instance, a HEPA filter for removing allergens, air droplets, dust and/or other contaminants in an environment. The filter 120 may include a removable filter portion for easy replacement.

The humidifier 122 may include a housing 113. The housing 113 may include a portion configured to removably couple to the housing 111 of the filter 120 and/or couple (e.g., directly) to the housing 110 of the fan module 102. The humidifier 122 may include one or more water reservoirs (not shown) and an assembly for dispersing water droplets/vapor into the air via air 144. The humidifier 122 may include circuitry (not shown) to output a desired amount of water vapor into an environment. In some cases, the humidifier 122 electrically couples via bus 146 to the controller 104. The humidifier 122 may receive signals from the controller 104 by way of the bus 146 to control the amount of water vapor output and the amount of time to output water vapor (e.g., based on a schedule). In an embodiment, relative humidity may be periodically measured and may be optionally displayed via an app on the user device 118 and/or on a display (not shown) provided by the housing 110. In response to humidity exceeding a predefined threshold, fan speed and/or the humidifier output may be adjusted to reach a target humidity (e.g., a user defined humidity level set via the app of the user device 118).

In some embodiments, and as shown, the humidifier 122 is not in fluid communication with the fan module 102. In this case, the humidified air 144 output by the humidifier 122 is external to the fan module 102. The humidified air 144 may then be received by the fan module 102 via intake ports 113-1 and 113-2 and/or intake ports 113-3 and 113-4 (in cases where the filter 120 is present). Thus, the growth of bacterial/mold on the motor and fan 108 may be eliminated as the fan simply receives filtered air rather than humidified air containing water droplets and/or air-borne contaminants which other integrated fan solutions utilize.

Figure 3:
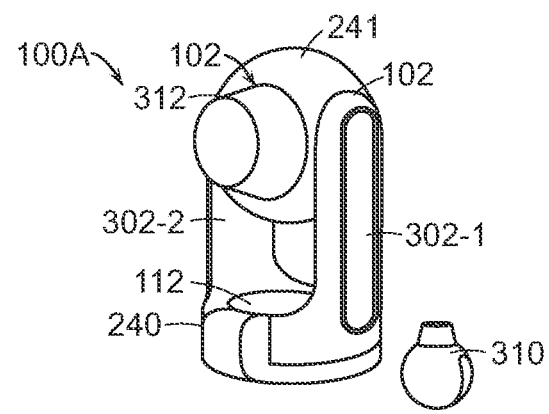
FIGS. 3-5 show an example configuration of an air treatment system in accordance with embodiments of the present disclosure.

The fan module 102 may further include additional circuitry 114. Additional circuitry 114 may include, for example, one or more image sensors/cameras. One example image sensor 312 is shown in FIG. 3. For example, the one or more image sensors may output color image data (RGB), color and depth image data (RGBD camera), depth sensor information, stereo camera information (L/R RGB), YUV, infrared signals, and so on. For example, the additional circuitry 114 may include a first sensor being an infrared detector and a second sensor being a color-image sensor (e.g., RGB, YUV). In one example, the fan module 102 includes a first image sensor configured for capturing an image signal (e.g., color image sensor, depth-enabled image sensing (RGBD), stereo camera (L/R RGB), YUV, infrared, and x-ray) and a second image sensor configured to capture image data different from the first image sensor.

In an embodiment, the fan module 102 compares image data received from the one or more image sensors to data within memory 105 to, for example, recognize a particular user present in an environment. In this embodiment, the controller 104 may implement a known facial recognition algorithm to recognize a user. In the event a user is recognized, the fan module 102 may automatically begin output of air 150 based on a user profile. The user profile may include a preferred fan speed, a preferred fragrance preference, and/or whether the fan module 102 should output air 150 directly at a recognized user's position in a room or not, as the case may be.

Note that this disclosure is not necessarily limited to tracking only "identified" users. For instance, in some cases the fan module 102 may pan/tilt, e.g., via the pan/tile mechanism 106, to move to follow any person in an environment as they move around.

In an embodiment, the image data processed by the fan module 102 may also include thermal (e.g., infrared) image data, as discussed above. In this embodiment, the fan module 102 may thermally map a room to identify areas of interest for cooling/heating purposes. For instance, if warm air is found to be in pockets (e.g., the corner of a ceiling), the fan module 102 may identify the spot and direct air flow in that general direction to bring the temperature down.

Figure 8:
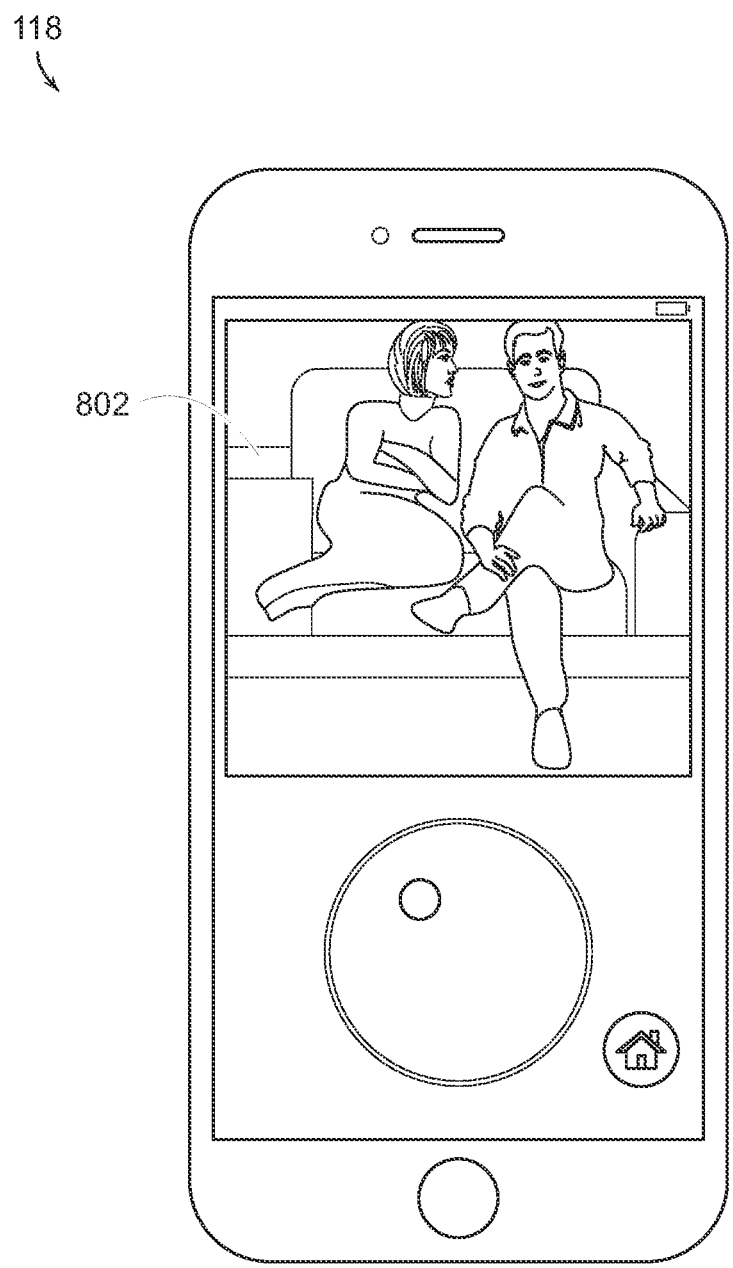
FIG. 8 shows thermal image data on a user device received from an air treatment system, in accordance with an embodiment of the present disclosure.

The thermal map may also extend to people/pets in a room. For example, the heat signature of a user may be utilized to determine if the fan module 102 should direct air in that user's direction. In this example, a person who appears relatively hot (e.g., having just come indoors on a hot summers day) may cause the fan module 102 to register the heat signature as needing cooling, e.g., based on a predefined threshold temperature, and direct air accordingly. In some cases, the fan module 102 provides the thermal data to the user device 118, such as shown in FIG. 8. In this case, the user may utilize the visualized thermal image data 802 to "train" the app in order to cause the fan module 102 to provide heating/cooling depending on a person's registered heat signature. The thermal image data sent to the user device 118 may also allow a user to recognize spots in their home/office where heat may be entering (e.g., via a crack, window, or other opening) or where heat/cold air is escaping. Such information may be useful for detecting and fixing leaks in an environment.

The additional circuitry may further include a microphone sensor for receiving voice input commands from a user. For example, the fan module 102 may receive voice commands such as "fan on" to cause the fan to begin circulating air in a surrounding environment. In another example, the fan module 102 may include a voice command such as "fan on me" to cause the fan to target (e.g., via rotation by pan/tilt mechanism 106) the user who spoke the command to direct air flow in their general direction. Likewise, "fan off me" or "fan move left/right/up/down" may further be suitable voice commands for adjusting operation of the fan module 102. Voice commands may also be utilized to change fan speed of the motor and fan 108 and/or may be utilized to select a particular output fragrance. The user may therefore utilize voice and/or other commands, e.g., commands executed via an app, to cause the air treatment system to switch from a semi-autonomous mode to a manual mode for a predefined period of time to ensure air circulation comports with a user's desired configuration.

In some cases, the user device 118 may receive/capture the voice commands via a local microphone and transmit the same to the fan module 102 to cause the same to change operation accordingly.

Figure 2:
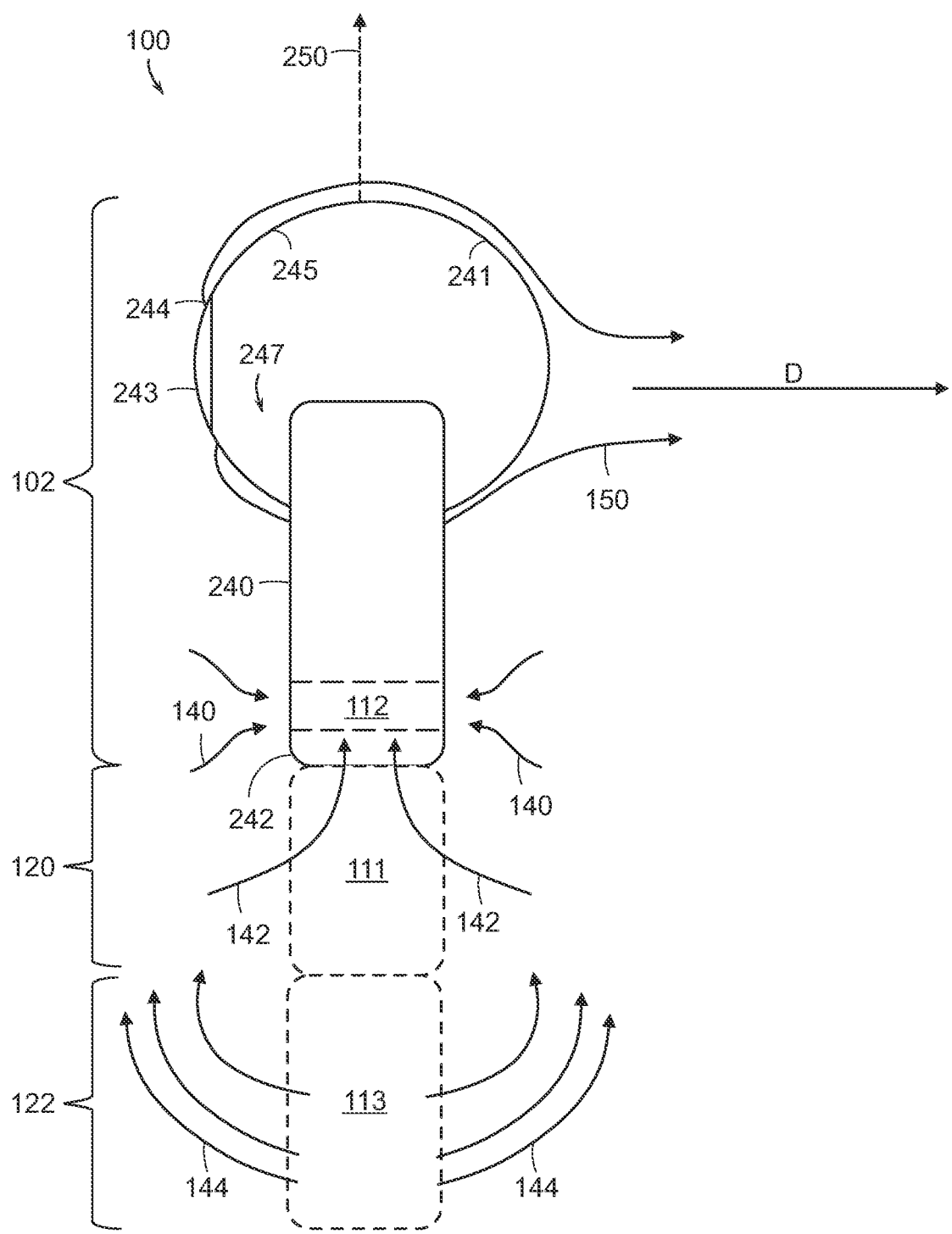
FIG. 2 shows another example block diagram of the example air treatment system of FIG. 1, in accordance with an embodiment of the present disclosure.

Turning to FIG. 2, a block diagram shows a side view of the air treatment system 100 in accordance with various aspects and embodiments of the present disclosure. As shown, the fan module 102 includes a housing comprised of a base portion 240 and a spheroid fan portion 241 (or fan body 241). In some embodiment, the base portion 240 includes at least two arms extending therefrom to hold the fan body 241 securely in position, which are better shown in FIGS. 3-5. However, the base portion 240 may include less arms, e.g., one arm as shown in the embodiment of FIGS. 14A-14G, or more than two arms depending on a desired configuration. A first end 242, or module coupling end, of the base portion 240 may include a coupling receptacle for coupling with the optional filter 120 and/or optional humidifier 122. A portion of the pant/title mechanism 106 may be disposed adjacent the module coupling end 242 and may allow the base 240, and by extension the fan body 241, to rotate about the longitudinal axis 250 (e.g., to provide movement/rotation along a horizontal axis).

A second end 247, or fan coupling end, of the base portion 240 may couple to the fan body 241. The fan body 241 may couple to base 240 by a second portion of the pan/title mechanism 106, with the second portion of the pan/title mechanism 106 allowing for up/down movement, or more particularly, movement along the longitudinal axis 250. Thus, the pan/tilt mechanism 106 of the fan module 102 allows for 360 degrees of movement to direct output air 150 towards virtually any location within an environment.

The fan body 241 is not necessarily limited to a sphere shape and may instead comprise any regular or irregular shape that provides at least one convex surface. For example, the fan body 241 may comprise an ellipsoid, oval or sphere, although these examples are not intended to be limiting.

In any event, the fan body 241 includes a nozzle 243 which defines at least one outlet 244, with the nozzle 243 being configured to output air 150 along convex surface 245. As shown, the Coanda effect results in air 150 generally following convex surface 245 such that the air is generally is substantially output in direction D. Accordingly, air 150 may travel externally and not necessarily through a passageway provided through the fan body 241. However, aspects and embodiments are equally applicable to nozzles that expel air through a passageway that extends substantially through the center of the fan body.

The intake 112 may be adjacent the module coupling end 242. The intake 112 may be fluidly coupled via one or more passageways within the base 240 which extend substantially in parallel with the longitudinal axis 250.

Figure 4:
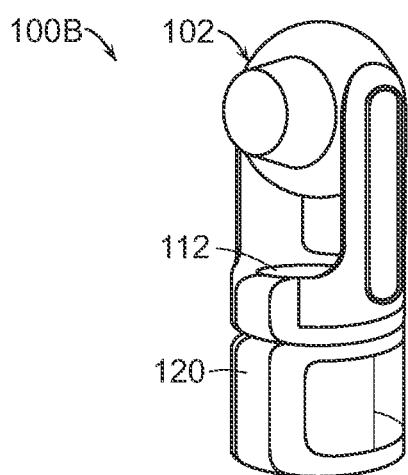
Figure 5:
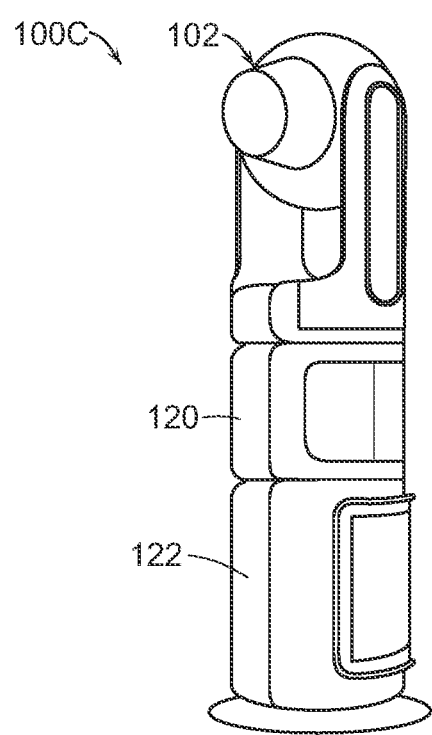

Referring to FIGS. 3-5 the air treatment system is shown in accordance with embodiments disclosed herein. FIG. 3 shows an air treatment system 100A including only the fan module 102. As shown, intake 112 includes at least one semi-permeable region (e.g., a mesh) to receive air, e.g., air 140. Air 140 may then be provided via passageways/channels in one or both of arms 302-1, 302-2 to the fan body 241. As shown, a fragrance unit 310 (or fragrance diffuser) may be placed on (or adjacent) the intake 112 and output an adjustable amount of fragrance towards the bottom of the fan body 241. Air, e.g., air 150, output by the nozzle 243 may then combine with the fragrance and thus cause air 150 to have a predefined scent. The fragrance unit 310 may include one or more scents (e.g., provided by oils or gels or fabrics impregnated with scent) which may be mixed, heated and/or blown (e.g., via a fan within the fragrance unit 310) to produce a desired fragrance at a desired intensity. The fragrance unit 310 may be powered by a battery. Alternatively, or in addition, the fragrance unit 310 may be powered by electric contacts located on the base 240. The fragrance unit 310 may be controlled via the controller 104.

In some cases, the fragrance unit 310 may include a battery and charger circuit to allow the unit to be "charged" via the base 240 and deposited in another location with an environment to operate independent of the base 240. The fragrance unit 310 may be remotely controlled via the user device 118 (or controlled indirectly by commands routed through the fan module 102).

Figure 6A:
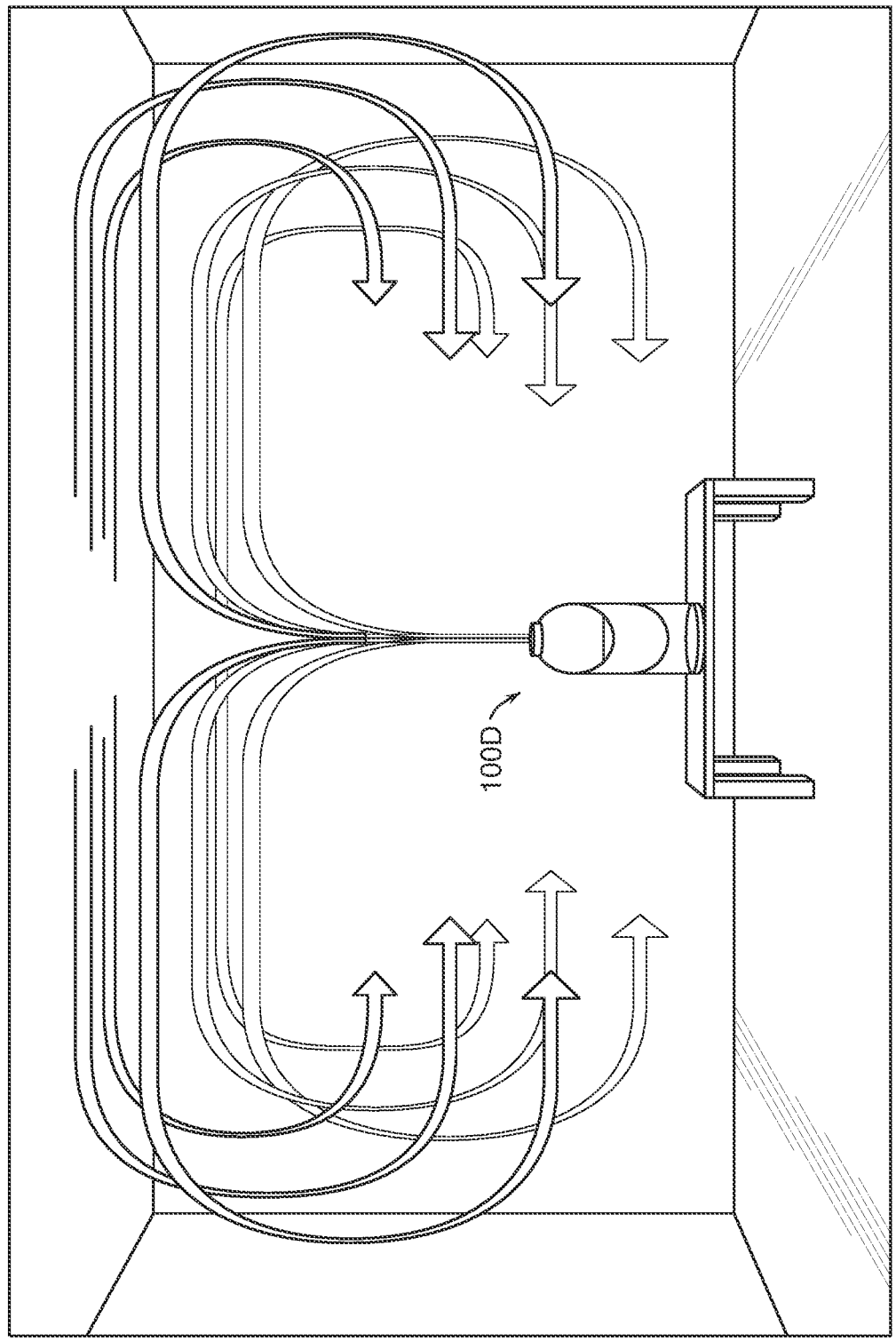
FIG. 6A shows an example air flow within an environment for an example air treatment system in accordance with an embodiment of the present disclosure.

FIG. 6A shows one example embodiment of an air treatment system 100D creating room-wide airflow. In an embodiment, the fan module may point directly/substantially upward and may use one or more image sensors to determine a center of the ceiling. Once determined, a convection current may be identified that circulates hot air and causes the same to normally stagnates adjacent the ceiling. The fan module 102 may efficiently target such hot/stagnate air and direct cooler air to disrupt the same. Thus, stratified layers of air of different temperatures may be mixed efficiently to circulate air fully through an environment.

Figure 6B:
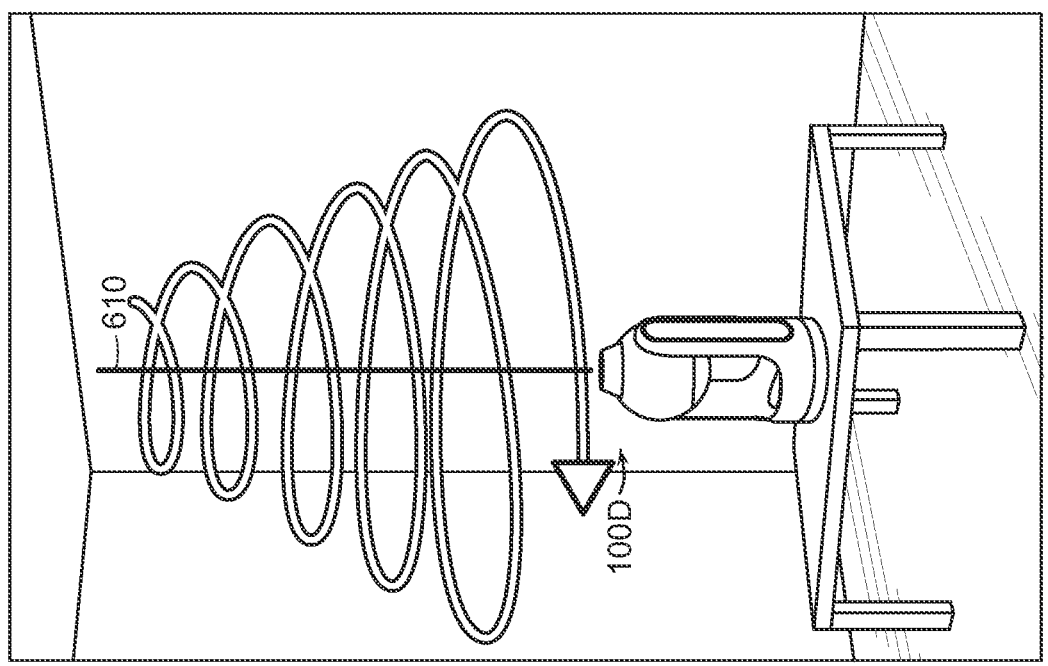
FIG. 6B shows an example air flow within an environment for an example air treatment system in accordance with an embodiment of the present disclosure.

As shown in FIG. 6B another example embodiment of an air treatment system 100D is shown. As shown, the fan module may move in a spiral fashion so as to force hot or stagnant/dirty air from the top layers of an airspace adjacent a ceiling. For example, the fan module may begin facing upwards towards the ceiling and then start by rotating in full continuous revolutions about the base vertical pan axis 610 while slowly tiling down from the upward-facing position. Thus, a spiral may be transcribed by a resulting air stream to force room air downward towards a filter of the air treatment system, for example.

Figure 7:
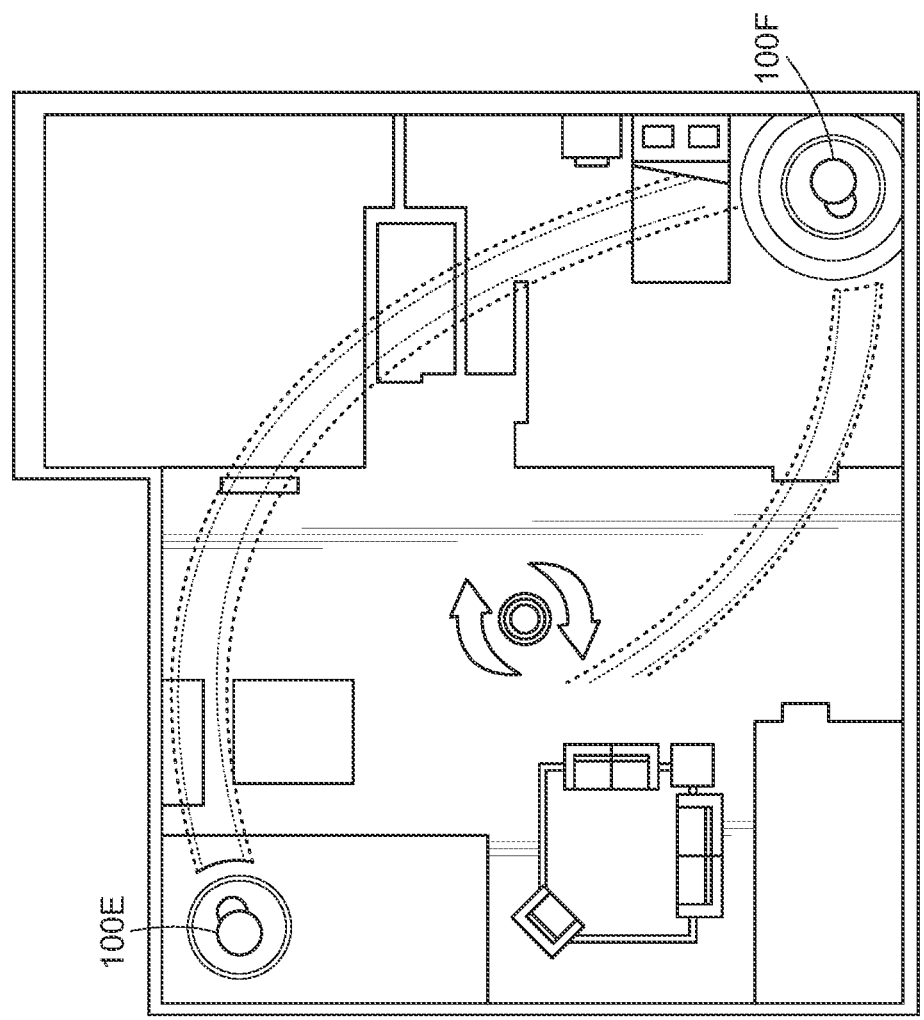
FIG. 7 shows an example of a plurality of air treatment systems communicating with each other in accordance with an embodiment of the present disclosure.

FIG. 7 shows an example embodiment where air treatment system 100E is in communication with air treatment system 100F to provide room-wide/environment-wide circulation. In this embodiment, each air treatments system may share their present direction with each other, e.g., via wireless connection 120, to ensure that their respective outputs are not directly pointed at each other, and instead covering different areas within the environment.

Figure 9:
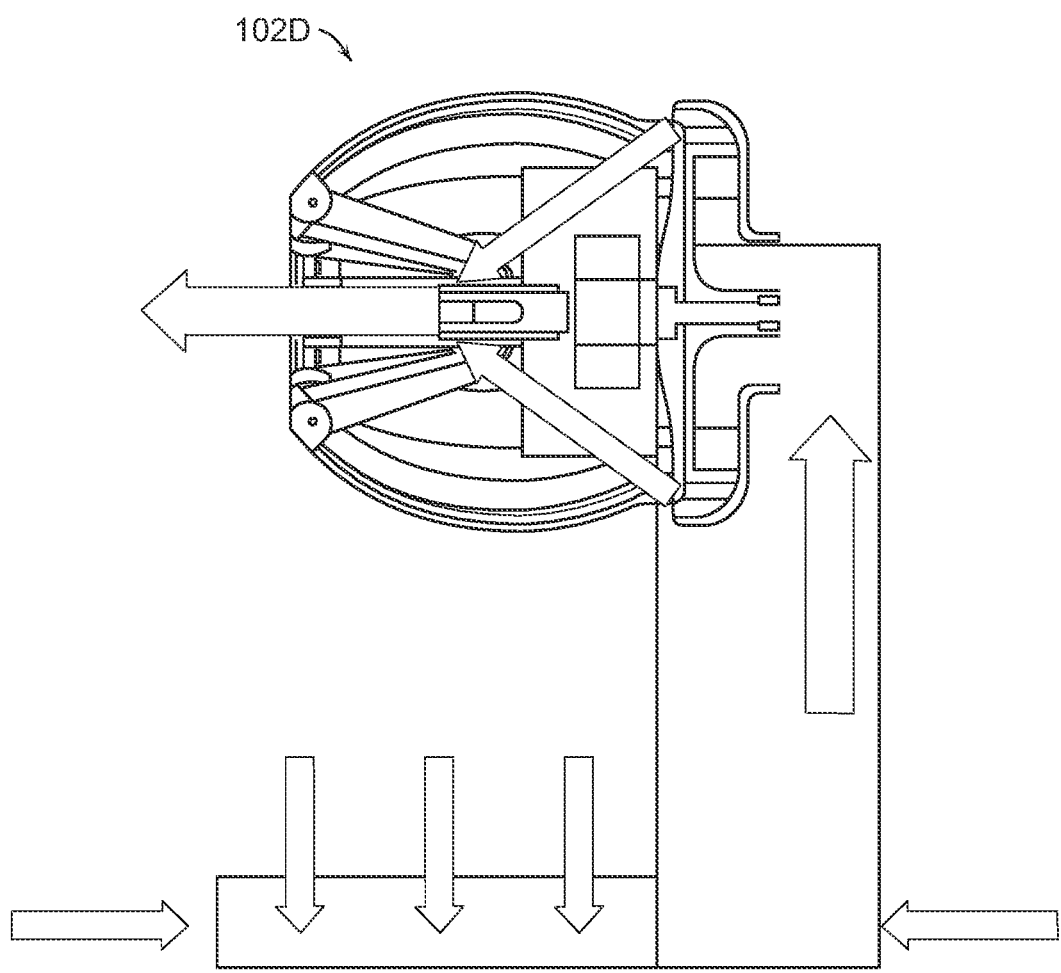
FIG. 9 shows another example embodiment of a fan module, in accordance with an embodiment of the present disclosure.

FIG. 9 shows an example embodiment of a fan module 102D in accordance with an aspect of the present disclosure. As shown, the air is taken in through the base, e.g., via intake 112, and brought up to the spheroid fan portion. A change over valve may then direct air through the spheroid fan portion.

Figure 10:
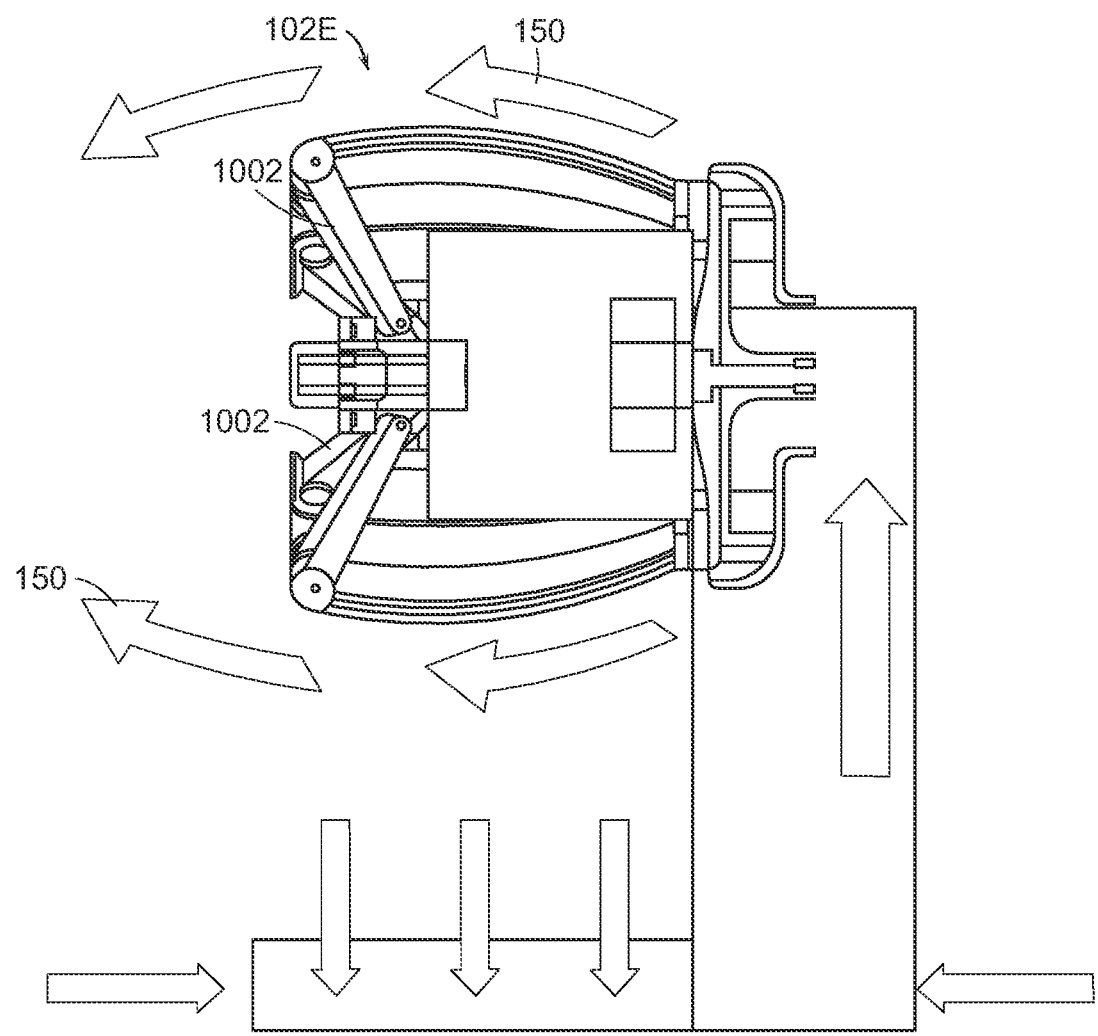
FIG. 10 shows another example embodiment of a fan module, in accordance with an embodiment of the present disclosure.

FIG. 10 shows another example embodiment of a fan module 102E. in this embodiment, hinged elements 1002 allow the spheroid fan portion to "open" similar to a flower to widen an air path for air 150.

Figure 11C:
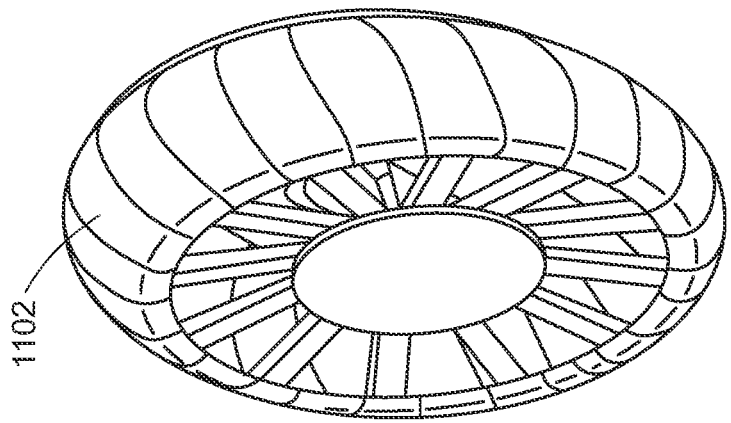
FIGS. 11A-11C shows a plurality of intermediate stages when widening an air path for the fan module of FIG. 10.
Figure 11B:
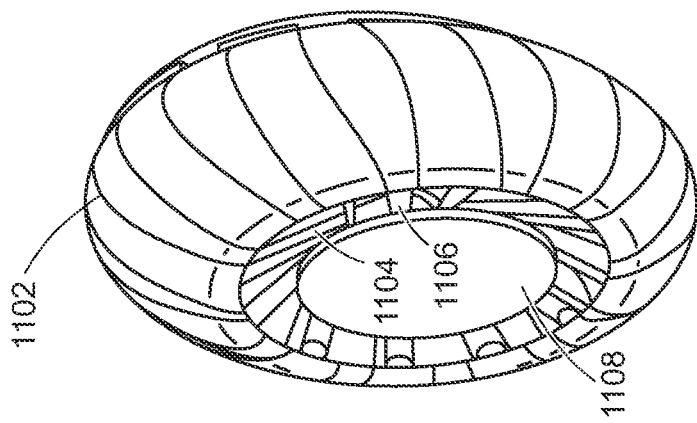
Figure 11A:
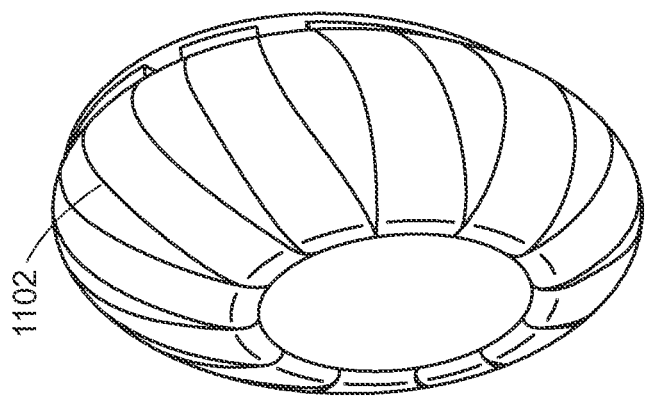

FIGS. 11A-11C show the module 102E of FIG. 10 during various stages of opening/closing. As shown, a stretchable material (e.g., fabric) surrounds the spheroid fan portion. A distal end of the hinged elements 1002 is coupled to a ring 1104 which is concentric about an axle 1106. As the ring 1104 travels towards the disc portion 1108 the spheroid shape widens by function of the hinged elements 1002 extending substantially orthogonal relative to the axle 1106. As shown in FIG. 11C, this results in a wider spheroid shape relative to the shape shown in FIG. 11A.

Figure 12A:
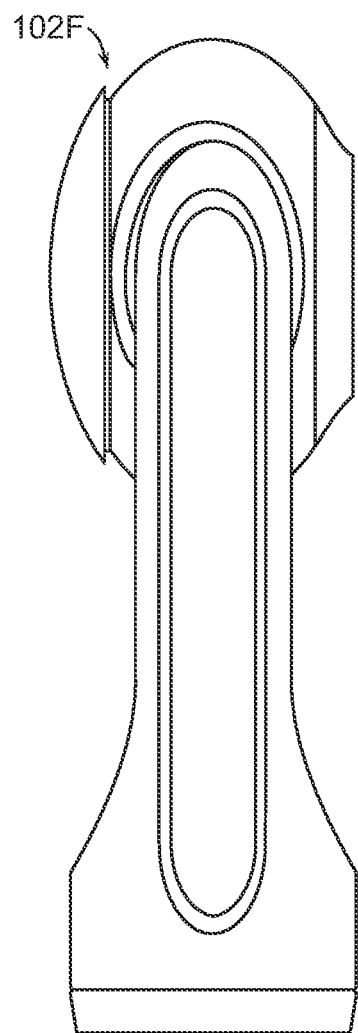
FIGS. 12A-12C show an additional example configuration for an air treatment system, in accordance with an embodiment of the present disclosure.
Figure 12B:
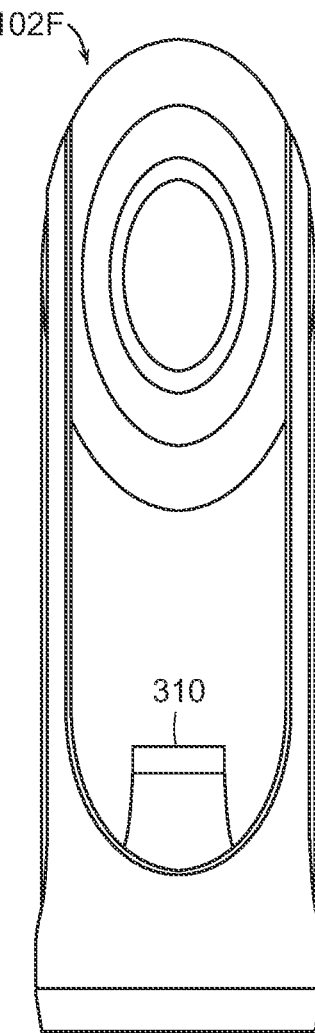
Figure 12C:
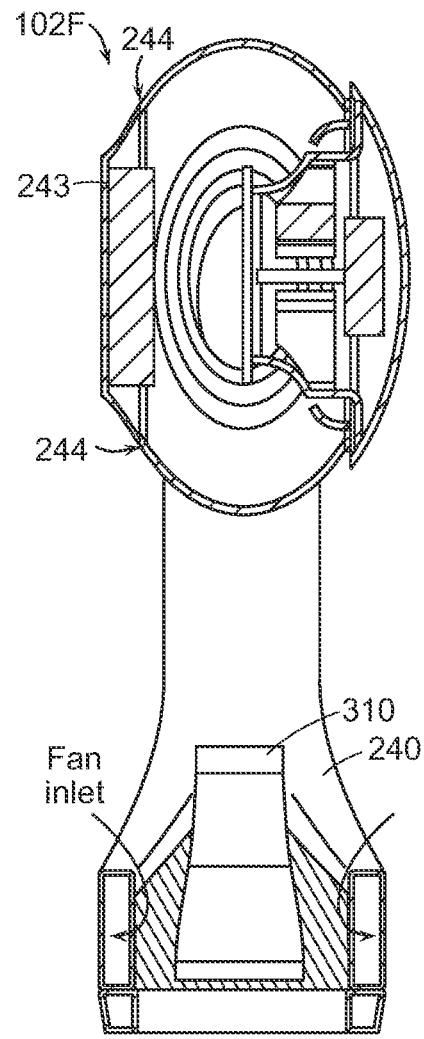
Figure 13A:
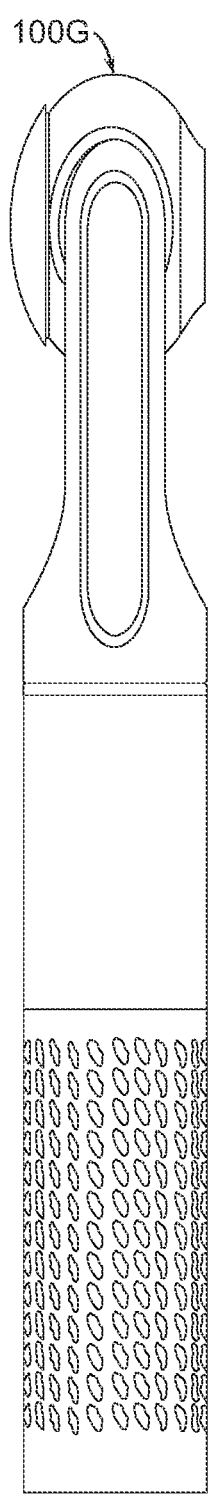
FIGS. 13A-13D show an additional example configuration for an air treatment system, in accordance with an embodiment of the present disclosure.
Figure 13B:
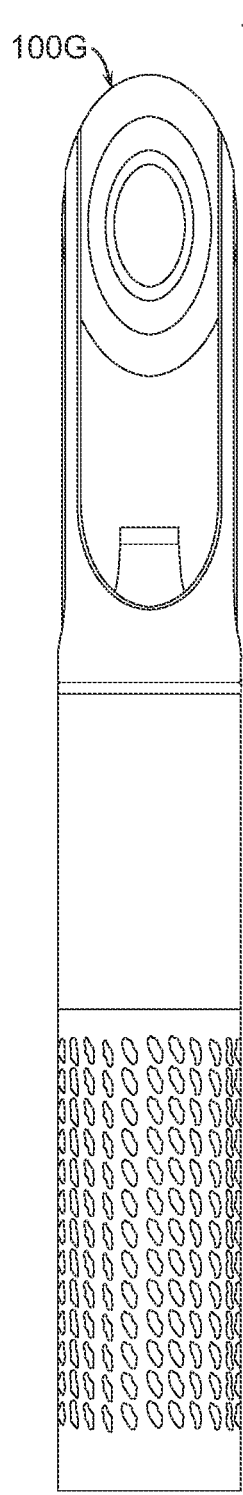
Figure 13C:
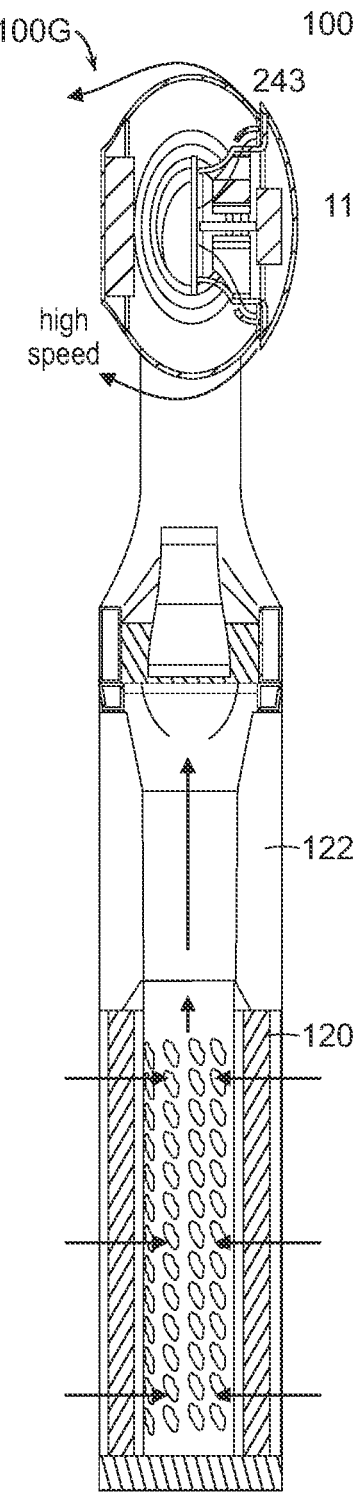
Figure 13D:
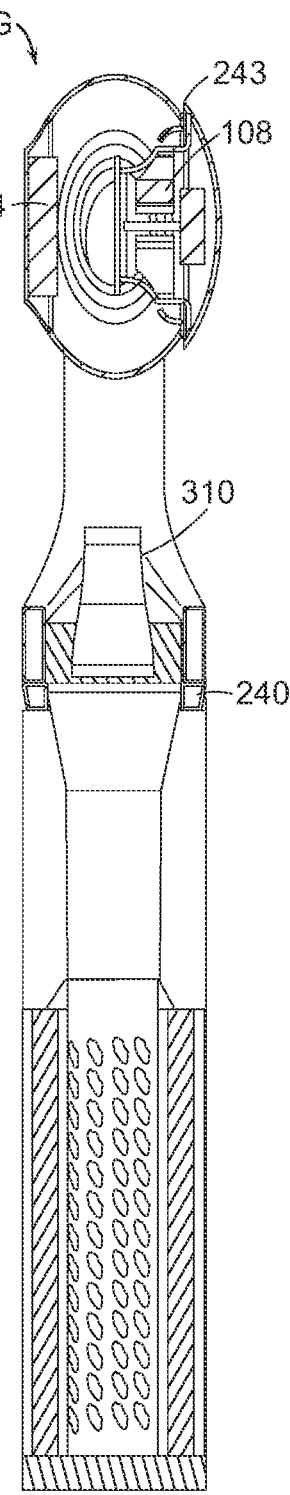
Figure 14A:
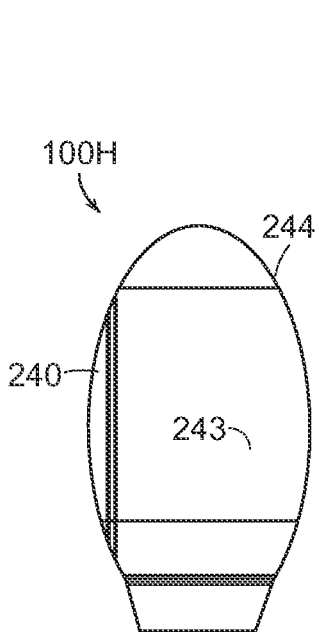
Figure 14B:
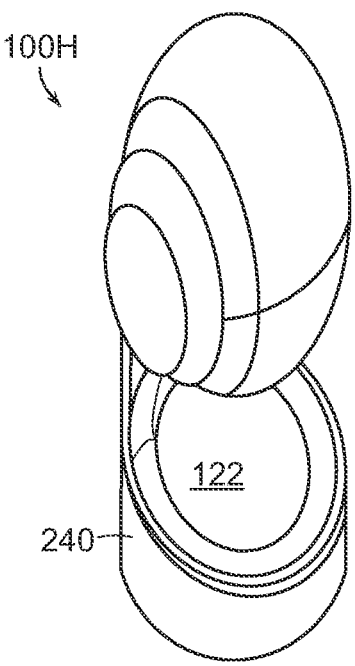
Figure 14C:
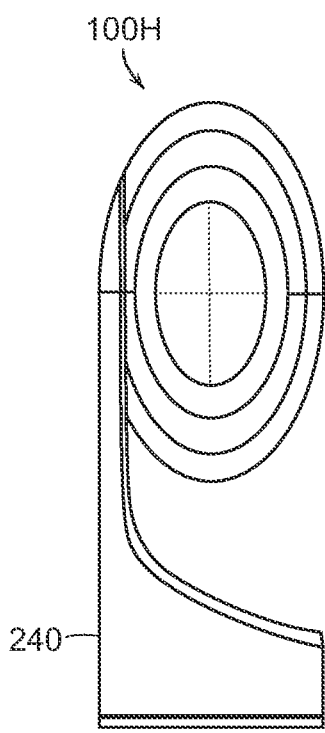
Figure 14D:
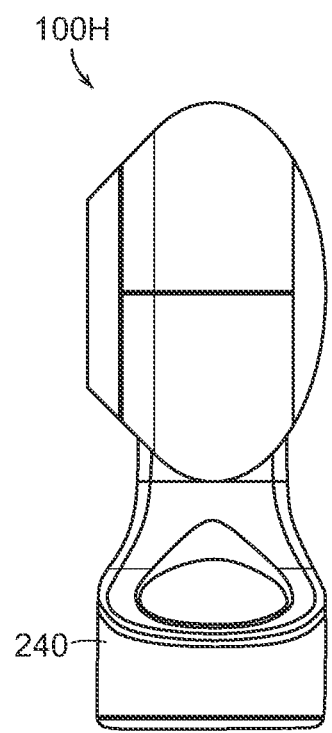

FIGS. 12A-12C show an additional configuration in accordance with aspects of the present disclosure. As shown, fan module 102F includes fan inlets within an opening of the base 240.

FIGS. 13A-13D show an additional configuration in accordance with aspects of the present disclosure. As shown, the air treatment system 100G includes an air filter 120 which is in fluid communication with base 240.

FIGS. 14A-14G show an additional configuration in accordance with aspects of the present disclosure. As shown, the air treatment system 100H includes a fan module with a single arm extending from base 240.

In accordance with an aspect of the present disclosure a modular air treatment system is disclosed. The air treatment system including a fan module, the fan module including, an intake having at least a first inlet to receive air, a motor to generate airflow based on the received air, a nozzle to output the generated airflow, the nozzle configured to rotate about a first rotational axis to direct the generated airflow at a region of interest in a surrounding environment, an air filter module to removably couple to the fan module, the air filter module having at least one output port to fluidly couple to first inlet of the fan module to provide filtered air, and a humidifier module to removably couple to the fan module and the air filter module, the humidifier module to output humidified air.

In accordance with an another aspect an air treatment system is disclosed. The air treatment system including a fan portion having a base, the fan portion including an intake to receive air from at least a first inlet, the first inlet disposed on a bottom surface of the base, a motor to generate airflow based on the air received by the intake, and a nozzle to output the generated airflow, the nozzle configured to rotate about a first and second rotational axis to direct the generated airflow at a region of interest in a surrounding environment, an air filter portion having a first end coupled to the bottom surface of the base and a second end to couple to a humidifier portion, the first end of the air filter portion having at least one output port fluidly coupled to first inlet of the fan portion to provide filtered air, and the humidifier portion coupled to the second end of the air filter portion, the humidifier portion to output humidified air.

In accordance with another aspect of the present disclosure an air treatment system is disclosed. The air treatment system including a fan portion, the fan portion including an intake to receive air from at least one of a first inlet and/or a second inlet, a motor to generate airflow based on the air received by the intake, a nozzle to output the generated airflow, the nozzle configured to rotate about at least a first rotational axis to direct the generated airflow at a region of interest in a surrounding environment, and a controller to cause the nozzle to rotate about the first rotational axis, an air filter portion to removably couple to the fan portion, the air filter portion having at least one output port to fluidly couple to the first inlet of the fan portion to provide filtered air, a humidifier portion to removably couple to the fan portion and the air filter portion, the humidifier portion to output humidified air based on a signal received from the controller of the fan portion, and means for switchably restricting air flow into the fan portion via the second inlet in response to the air filter portion removably coupling to the fan portion.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. It will be appreciated by a person skilled in the art that an air treatment system may embody any one or more of the features contained herein and that the features may be used in any particular combination or sub-combination. Modifications and substitutions by one of ordinary skill in the art are considered to be within the scope of the present disclosure, which is not to be limited except by the following claims.

What is claimed is:

1. A modular air treatment system comprising:
    a fan module, the fan module including:
        an intake having at least a first inlet to receive air;
        a motor to generate airflow from the received air; and
        a fan body having a first side, a second side, and a nozzle to output generated airflow at the first side such that the generated airflow travels to the second side, the nozzle being configured to rotate about a first rotational axis to direct the generated airflow from the second side of the fan body toward a region of interest in a surrounding environment;
    an air filter module removably coupled to the fan module, the air filter module having at least one output port fluidly coupled to the first inlet of the fan module to provide filtered air directly from the air filter module to the first inlet of the fan portion; and
    a humidifier module having a first side separably connected to the fan module and a second side separably connected to the air filter module, the humidifier module having an outlet configured to output humidified air from the humidifier module directly outside of the modular air treatment system.

2. The modular air treatment system of claim 1, wherein the intake further comprises a second inlet, and when the air filter module is removably coupled to the fan module, a flow of humidified air generated by the humidifier module is output external to the modular air treatment system.

3. The modular air treatment system of claim 1, wherein the fan module, the air filter module and humidifier module are coupled end-to-end and collectively form a vertical stack configuration.

4. The module air treatment system of claim 1, wherein the air filter module includes a bus electrically coupled to the fan module, and wherein the humidifier module is electrically coupled to the fan module by way of the bus provided by the air filter module.

5. The module air treatment system of claim 4, wherein the fan module further includes a controller to provide a signal via the bus to the humidifier module to control an amount of humidified air output by the humidifier module.

6. The modular air treatment system of claim 1, wherein the fan module further includes a pan and tilt mechanism to cause the nozzle to rotate about at least the first rotational axis and a second rotational axis to reposition and direct air in a selected direction.

7. The modular air treatment system of claim 1, wherein the fan module includes a network interface module, and wherein the fan module is configured to adjust operation based on wireless communications received via the network interface module from a user device.

8. The modular air treatment system of claim 1, wherein the fan module includes an image sensor configured to output thermal image data, and wherein the fan module determines what direction to provide output air based at least in part on the thermal image data.

9. The modular air treatment system of claim 1, wherein the fan module includes an image sensor configured to output image data, and wherein the fan module is configured to identify at least one user in an environment based on the image data.

10. The modular air treatment system of claim 9, wherein the at least one user is identified based on a facial recognition algorithm.

11. The modular air treatment system of claim 9, wherein the fan module is configured to adjusts at least one operational parameter based on a user profile associated with the at least one identified user.

12. The modular air treatment system of claim 11, wherein the at least one operational parameter comprises a fan speed, an output direction for output air, and/or an output fragrance.

13. The modular air treatment system of claim 1, further comprising a fragrance diffuser configured to produce at least one predefined fragrance.

14. The modular air treatment system of claim 13, wherein the fragrance diffuser electrically couples to the fan module.

15. An air treatment system comprising:
a fan portion having a base and a fan body, the fan portion including:
an intake to receive air from at least a first inlet, the first inlet disposed on a bottom surface of the base;
a motor to generate airflow from the air received by the intake; and
a nozzle to output generated airflow adjacent a first side of the fan body such that the generated airflow travels to a second side of the fan body, the nozzle being configured to rotate about a first and second rotational axis to direct the generated airflow from the second side of the fan body toward a region of interest in a surrounding environment;
an air filter portion having a first end coupled to the bottom surface of the base and a second end, the first end of the air filter portion having at least one output port fluidly coupled to the first inlet of the fan portion to provide filtered air directly from the air filter portion to the first inlet of the fan portion; and
a humidifier portion separably coupled to the second end of the air filter portion, the humidifier portion having an outlet to output humidified air from the humidifier module directly outside of the modular air treatment system.

16. The air treatment system of claim 15, wherein the intake further comprises a second inlet, and when the air filter portion is removably coupled to the fan portion, a flow of humidified air generated by the humidifier portion is output external to the modular air treatment system.

17. The air treatment system of claim 15, wherein the fan portion, air filter portion and humidifier portion are configured to couple together and form a vertical stack configuration.

18. The air treatment system of claim 15, wherein the air filter portion includes a bus electrically coupled, to the fan portion, and wherein the humidifier portion electrically couples to the fan portion by way of the bus provided by the air filter portion.

19. An air treatment system, the air treatment system comprising:
a fan portion, the fan portion including:
an intake to receive air from at least one of a first inlet and/or a second inlet;
a motor to generate airflow from the air received by the intake;
a fan body;
a nozzle to output generated airflow adjacent a first side of the fan body such that the generated airflow travels to a second side of the fan body, the nozzle being configured to rotate about a first rotational axis to direct the generated airflow from the second side of the fan body toward a region of interest in a surrounding environment; and
a controller to cause the nozzle to rotate about the first rotational axis;
an air filter portion removably coupled to the fan portion, the air filter portion having at least one output port to fluidly couple to the first inlet of the fan portion to provide filtered air directly to the first inlet of the fan portion, wherein the second inlet is mechanically closed as the air filter portion is removably coupled to the fan portion; and
a humidifier portion having one side separably connected to the fan portion and the air filter portion, the humidifier portion configured to output humidified air via an outlet based on a signal received from the controller of the fan portion, wherein humidified air from the humidifier portion is output directly outside of the air treatment system via the outlet.

20. The air treatment system of claim 19, further comprising means for identifying a user within the surrounding environment and adjusting operation of the air treatment system based on the identified user.

* * * * *